United States Patent
Salgaonkar et al.

(10) Patent No.: US 11,911,215 B2
(45) Date of Patent: Feb. 27, 2024

(54) ULTRASOUND PROBE WITH ADJUSTABLE APERTURE

(71) Applicant: Siemens Medical Solutions USA, Inc., Malvern, PA (US)

(72) Inventors: Vasant Salgaonkar, Sunnyvale, CA (US); Lex J. Garbini, Renton, WA (US); William R. Dreschel, State College, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 17/303,295

(22) Filed: May 26, 2021

(65) Prior Publication Data

US 2022/0378399 A1 Dec. 1, 2022

(51) Int. Cl.
*A61B 8/00* (2006.01)
*A61B 1/00* (2006.01)
*A61B 8/12* (2006.01)
*B06B 1/06* (2006.01)

(52) U.S. Cl.
CPC ............... *A61B 8/445* (2013.01); *A61B 8/12* (2013.01); *A61B 8/4494* (2013.01); *A61B 1/00082* (2013.01); *B06B 1/0607* (2013.01)

(58) Field of Classification Search
CPC ......... A61B 8/445; A61B 8/12; A61B 8/4494; A61B 1/00082; A61B 2017/22045; A61B 2090/3782; A61B 2017/22038; A61B 8/00; A61B 8/08; A61B 8/0883; A61B 8/4483; A61B 8/4444; A61B 8/4477; B06B 1/0607; B06B 1/0622; A61F 2/2433; A61M 2039/0235; A61M 25/0074; A61M 25/10; A61M 25/1036; A61M 25/1038; G06T 2207/30021; A61N 7/00; A61N 2007/0043; A61N 2007/0052; A61N 2007/0078; A61N 2007/0091; A61N 2007/0095

See application file for complete search history.

(56) References Cited

U.S. PATENT DOCUMENTS

| | | | | |
|---|---|---|---|---|
| 5,257,628 A | * | 11/1993 | Ishiguro | A61B 8/445 600/463 |
| 5,295,486 A | * | 3/1994 | Wollschlager | A61B 5/352 600/447 |
| 5,513,639 A | * | 5/1996 | Satomi | A61B 8/12 |
| 5,605,154 A | | 2/1997 | Ries et al. | |
| 7,500,954 B2 | | 3/2009 | Wilser et al. | |
| 7,544,166 B2 | | 6/2009 | Yuan et al. | |
| 8,636,664 B2 | | 1/2014 | Brannan | |
| 8,864,675 B2 | | 10/2014 | Dietz et al. | |
| 8,959,753 B2 | * | 2/2015 | Garbini | A61B 6/12 29/721 |
| 10,625,046 B2 | | 4/2020 | Fabro | |
| 2003/0004439 A1 | | 1/2003 | Pant et al. | |

(Continued)

*Primary Examiner* — Sean D Mattson
*Assistant Examiner* — Michael Yiming Fang

(57) ABSTRACT

For intraluminal ultrasound probes, the transducer is divided into multiple segments. The segments are connected in a way that allows them to slide relative to each other. This sliding arrangement allows for the transducer to be used in two different apertures at different times while in the patient. One aperture is shaped for insertion of the probe through a limited space, and the other aperture forms an array with a larger elevation extent, allowing greater quality imaging along the elevation dimension.

16 Claims, 4 Drawing Sheets

(56) References Cited

U.S. PATENT DOCUMENTS

| | | | |
|---|---|---|---|
| 2007/0078345 A1* | 4/2007 | Mo | G10K 11/32 |
| | | | 600/459 |
| 2010/0262013 A1 | 10/2010 | Smith et al. | |
| 2012/0095347 A1 | 4/2012 | Adam et al. | |
| 2012/0287750 A1* | 11/2012 | Deladi | A61B 5/0084 |
| | | | 367/7 |
| 2013/0199019 A1* | 8/2013 | Garbini | A61B 6/485 |
| | | | 29/729 |
| 2015/0045668 A1* | 2/2015 | Smith | A61B 8/4218 |
| 2018/0130457 A1 | 5/2018 | Hakkens et al. | |
| 2019/0046159 A1* | 2/2019 | Smith | A61B 5/6847 |
| 2021/0108866 A1* | 4/2021 | Lucht | H01L 23/3672 |
| 2022/0000450 A1* | 1/2022 | Qiu | A61B 8/085 |
| 2022/0071476 A1* | 3/2022 | Kinomoto | A61B 8/4483 |
| 2022/0117584 A1* | 4/2022 | Haider | A61B 8/4494 |
| 2022/0226114 A1* | 7/2022 | Hou | A61B 8/4494 |

* cited by examiner

ULTRASOUND PROBE WITH ADJUSTABLE APERTURE

BACKGROUND

The present embodiments relate to intraluminal ultrasound probes, such as an intracardiac echo (ICE) catheter, endocavity probe, transesophageal probe, or gynecological probe. Infraluminal ultrasound probes capable of imaging a volume or multiple planes may not provide the desired image quality in all imaging planes or directions. Due to being on a long, thin probe or shaft for insertion into a lumen, the transducers are long and thin. For example, an ICE catheter may have a multi-dimensional transducer with a long rectangular shape (e.g., 7-23 mm×2-4 mm) to enable vascular access. The quality of imaging in the 2-4 mm dimension is less than for the 7-23 mm dimension. As another example, an ICE catheter includes a helically twisted array to allow volumetric imaging about the catheter axis, but at a reduced image quality.

SUMMARY

By way of introduction, the preferred embodiments described below include methods, systems, and improvements for intraluminal ultrasound probes. The transducer is divided into multiple segments. The segments are connected together in a way that allows them to slide relative to each other. This sliding arrangement allows for the transducer to be used in two different apertures at different times while in the patient. One aperture is shaped for insertion of the probe through a limited space, and the other aperture forms an array with a larger elevation extent, allowing greater quality imaging along the elevation dimension. The quality along the elevation dimension may be comparable to the quality in the azimuth dimension.

In a first aspect, an ultrasound probe is provided for ultrasound imaging. A housing is configured for insertion into a patient. The housing has an expandable portion. A guide is within the housing. A first two-dimensional array of elements connects with the guide. A second two-dimensional array of elements connects with the guide. The first two-dimensional array is slidable along the guide relative to the second two-dimensional array to form first and second imaging apertures of the ultrasound imaging while the housing and the first and second two-dimensional arrays are within the patient.

In a second aspect, an ultrasound array is provided for a catheter or intraluminal probe. A housing is configured for insertion into a patient. A plurality of multi-element transducers is slidable relative to each other within the housing. The multi-element transducers are configurable in first and second imaging apertures while within the patient. The first imaging aperture is shaped differently than the second imaging aperture. The first imaging aperture is formed by sliding from the transducers arranged in the second imaging aperture.

In a third aspect, a method is provided for ultrasound imaging. An intraluminal probe is inserted into a patient. The intraluminal probe includes at least two sub-arrays. Using at least one of the two sub-arrays as a first aperture extending mostly along a length of the intraluminal probe, the patient is imaged. The two sub-arrays are adjacent to each other along the length of the intraluminal probe. The two sub-arrays are rearranged into a second aperture while within the patient. The two sub-arrays are used as the second aperture for imaging the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An endoluminal probe, such as an ICE catheter, has an adjustable aperture for volume and/or multi-planar imaging. Conventional dimensions are provided for one aperture for advancing through the vasculature or lumen. The transducer has moveable transducer segments that may then be arranged inside a cardiac or other chamber to form a square-like or volume imaging profile (wider than for insertion). The probe may be long, thin and flexible for ease of intraluminal insertion and placement, and the retractable transducer segments may create a more square-like profile for 3D volume imaging when inside a cardiac chamber. A wide, squarer matrix transducer, similar to a transesophageal probe, may be provided through narrow and tortuous vascular pathways. The wider aperture may provide more balanced images in orthogonal planes.

In one embodiment, the ultrasound transducer segments can slide relative to each other. For endoluminal or ICE interventions, a long, thin and flexible form factor of the transducer is provided for lumen access. During insertion, the array is used for imaging to guide insertion while in the longer, narrow configuration. The transducer may be reorganized to a more square-like profile when positioned inside the heart, bladder, gastro-intestinal tract, etc. This reorganization increases effective aperture size and creates a more symmetric (e.g., square) shape for high-quality multiplane and/or 3D imaging. The probe housing may include an expandable sidewall, such as a balloon, for deploying the symmetric shaped aperture.

In another embodiment, the transducer segments may slide between the different apertures. Spring or superelastic-alloy (e.g., nitinol) interconnects provide for returning the aperture to the long and narrow configuration for withdrawal. The segmentation of the transducer may allow for less stiffness as compared to the transducer without segments.

In structural heart procedures, transesophageal (TEE) three-dimensional (3D) ultrasound imaging is used. TEE requires general anesthesia and an on-site echo-cardiographer in addition to the interventional cardiologist. ICE reduces this is to a one-doctor procedure, but with more limited volume imaging capability. By providing a 3D ICE catheter with a matrix-like transducer having about 1:1 aspect ratio, consistent 3D imaging across all scan planes is provided. About is used to allow for 20% tolerance. For insertion, the ICE catheter is no wider than 3-5 mm. The slidable transducer segments allow for both the desired volume imaging aspect ratio and imaging along a plane for insertion.

Figure 1:
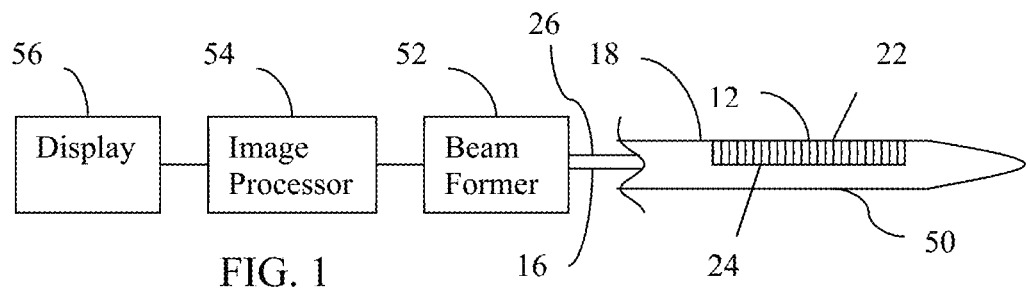
FIG. 1 is a block diagram of one embodiment of an ultrasound system for intraluminal imaging.

FIG. 1 shows a system for medical ultrasound imaging with a medical ultrasound probe. The ultrasound imaging system is used for diagnosis and/or treatment. The ultrasound probe is an intraluminal probe, such as a catheter. The ultrasound probe is used for ultrasound imaging using different apertures formed by mechanically rearranging the ultrasound array 12. The different apertures may be used for imaging the patient, such as one aperture using for imaging during insertion into or through the patient and the other used for volume imaging in a chamber.

The ultrasound imaging system includes the array 12 of elements 24 for medical ultrasound, a beamformer 52, an image processor 54, and a display 56. Additional, different, or fewer components may be provided. For example, the system includes the array 12 in an intraluminal probe 18 without the beamformer 52, image processor 54, and/or display 56. These imaging electronics may be in a separate ultrasound imaging system. The transducer array 12 and intraluminal probe 18 releasably connect with the imaging system. As another example, the beamformer 52 and/or image processor 54 may be integrated on a chip or chips with or adjacent to the array 12.

The array 12 connects to the beamformer 52 by the conductors 16 for imaging. The beamformer 52 includes a plurality of channels for generating transmit waveforms and/or receiving signals. Relative delays and/or apodization focus the transmit waveforms or received signals for forming beams. The beamformer 52 connects with the conductors 16. The beamformer 52 selects an aperture including one, some, or all of the elements 24 of the array 12. Different apertures may be used at different times.

The intraluminal probe 18 includes a housing 50, the array 12 of elements 24, the conductors 16, and one or more guide wires 26. Additional, different, or fewer components may be provided. For example, a port or tube for inserting and/or withdrawing fluid from the housing 50 is included. As another example, one or more markers for position determination are included.

The electrical conductors 16 connect the elements 24 of the array 12 to the receive beamformer 52. The conductors 16 are cables, coaxial cables, traces on flexible circuit material, wires, flex circuits, wire jumpers, combinations thereof, or other now known or later developed conductor. One conductor 16 is provided for each element 24. Alternatively, fewer conductors 16 than elements 24 may be used, such as for switched apertures, partial beamforming, or multiplexing The housing 50 is a sleeve of plastic or other material for insertion into a patient. For example, the housing 50 is formed from Pebax. Other materials, such as other Nylons or biologically neutral (or biocompatible) materials, may be used. The housing 50 is sealed over the array 12 to separate fluids of the patient from the interior of the probe 18.

The housing 50 is configured for insertion into a patient. In general, the housing 50 is cylindrical in shape, such as a long, thin tube. The housing 50 may be stiff, rigid, flexible, and/or semi-flexible. The housing 50 is shaped and sized to form the insertable portion of the intraluminal probe 18. For example, the housing 50 forms a catheter, TEE, transurethral probe, or endovaginal probe. Examples herein will be for a catheter, but the slidable sub-arrays may be used in various other intraluminal probes 18. In another embodiment, the probe 18 and corresponding housing 50 form a mirco-TEE for pediatric applications. The probe 18 is for imaging or for therapeutic application, such as being used to apply high intensity focused ultrasound (HIFU).

In one embodiment, the housing 50 forms an ICE catheter with the array 12. The array 12 may fit within 10 French (3.33 mm), 12.5 French, or another diameter catheter. The conductors 16 are routed through the catheter to the beamformer 52. The catheter transducer is used for imaging. The images assist in diagnosis, catheter or tool guidance, and/or therapy placement.

Figure 2:
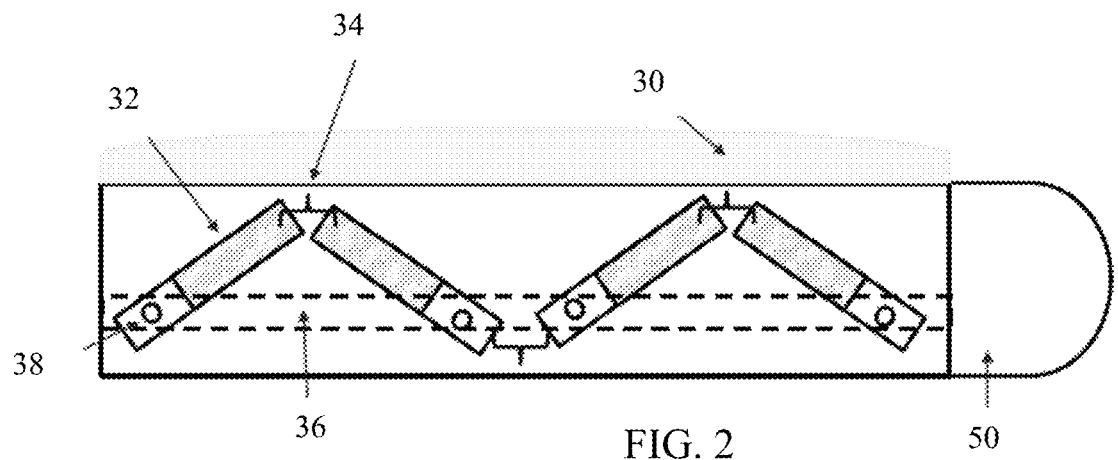
FIG. 2 illustrates one embodiment of a cross-sectional top view of a catheter with a segmented transducer.

In one embodiment shown in FIG. 2, the housing 50 includes an expandable portion 30. The expandable portion 30 is on one side of the probe 18 for any length along the longitudinal axis of the probe 18. For example, the expandable portion is about ⅓ to ½ of the circumference of the probe 19 and for a length about (e.g., within 10%) the same as the length of the array 12. The expandable portion is a balloon, rubber, or other material allowing stretching or expanding before or as the array 12 is reconfigured. The expandable portion 30 is adjacent to the array 12. In other embodiments, the housing 50 is expandable without having a separate region of different material for expansion.

The expandable portion 30 allows for the housing 50 to be inserted through a lumen without expansion and then expanding within a cavity or lumen in the patient. The array 12 may mechanically form two or more different apertures, one for use without expansion by the expandable portion 30 and one that expands or fits within the housing 50 due to expansion by the expandable portion 30.

The reconfiguration of the array 12 may cause expansion, such as stretching the housing 50 at the expandable portion. Alternatively, the expandable portion 30 is expanded to allow reconfiguration of the array 12. For example, a fluid channel injects or withdraws saline or other fluid from within the housing 50 adjacent to the expandable portion 30 to expand or deflate. The inflation of the expandable portion 30 may help hold the probe 18 in place in an orifice, such as the inflated balloon of the expandable portion 30 locking the probe 18 in place at the urethral orifice (e.g., against the urethra) for bladder imaging.

The array 12 has a plurality of elements 24, backing block, electrodes, and a matching layer. Additional, different, or fewer components may be provided. For example, two or more matching layers are used.

The elements 24 may contain piezoelectric material. Solid or composite piezoelectric materials may be used. Each element is a rectangular solid, cube, or six sided, but other surfaces may be provided. For example, the emitting face of one or more elements 24 is concave or convex for elevation focusing or frequency-based directivity. The elements may be merged into a backing block. Alternatively, a microelectromechanical device, such as a flexible membrane, is used. Any now known or later developed ultrasound transducer may be used.

Any number of elements 24 may be provided, such as ten, hundreds, or thousands of elements. For larger numbers of elements, one or more sub-array beamformers may be included, such as flip-chip-mounted to a back of the array 12. The elements 24 are adjacent to each other, such as having substantially wavelength or less spacing between the centers of adjacent elements 24.

Figure 3:
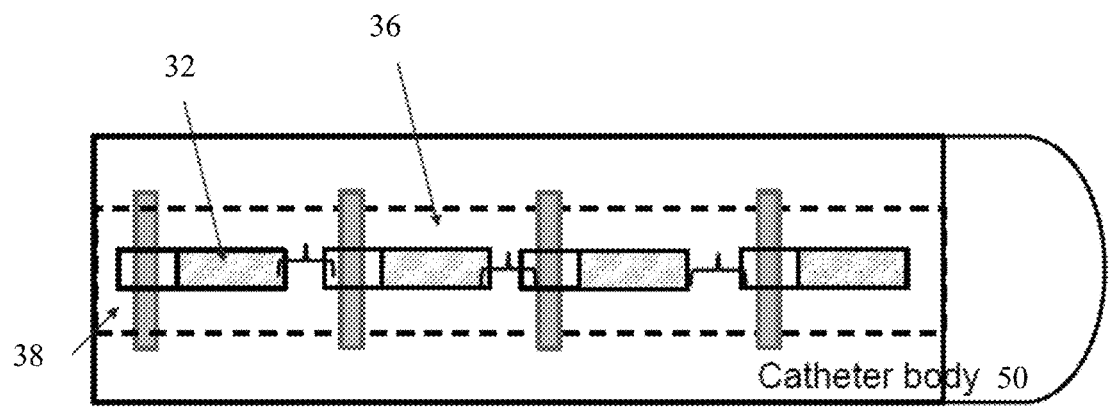
FIG. 3 illustrates a cross-sectional side view of the embodiment of FIG. 2.
Figure 4:
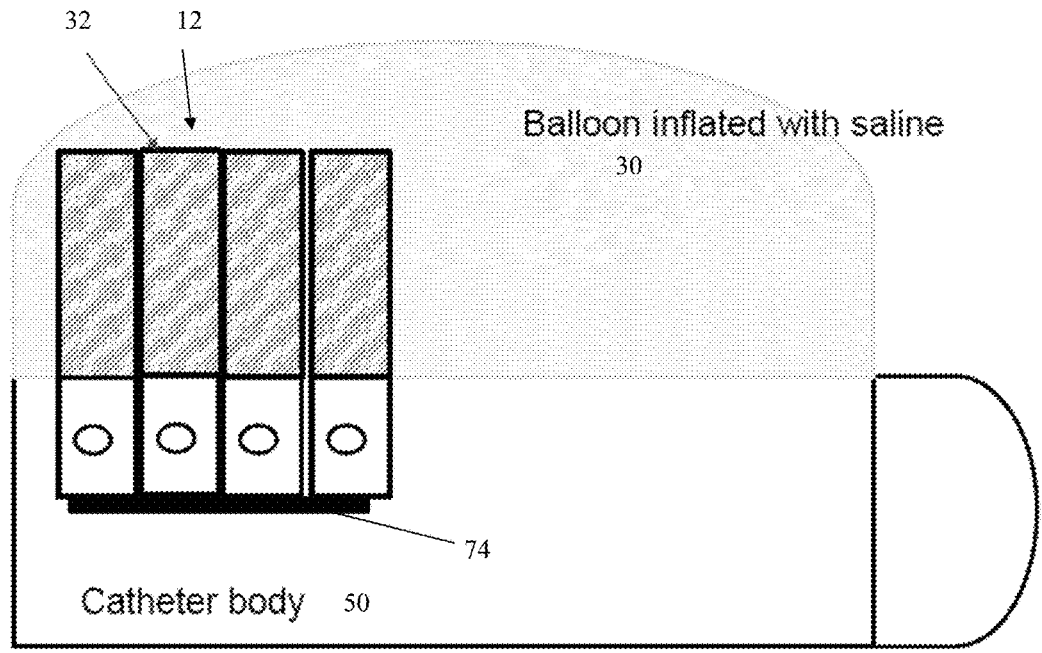
FIG. 4 illustrates the catheter of FIG. 2 with the segmented transducer arranged in a volume imaging aperture.
Figure 5:
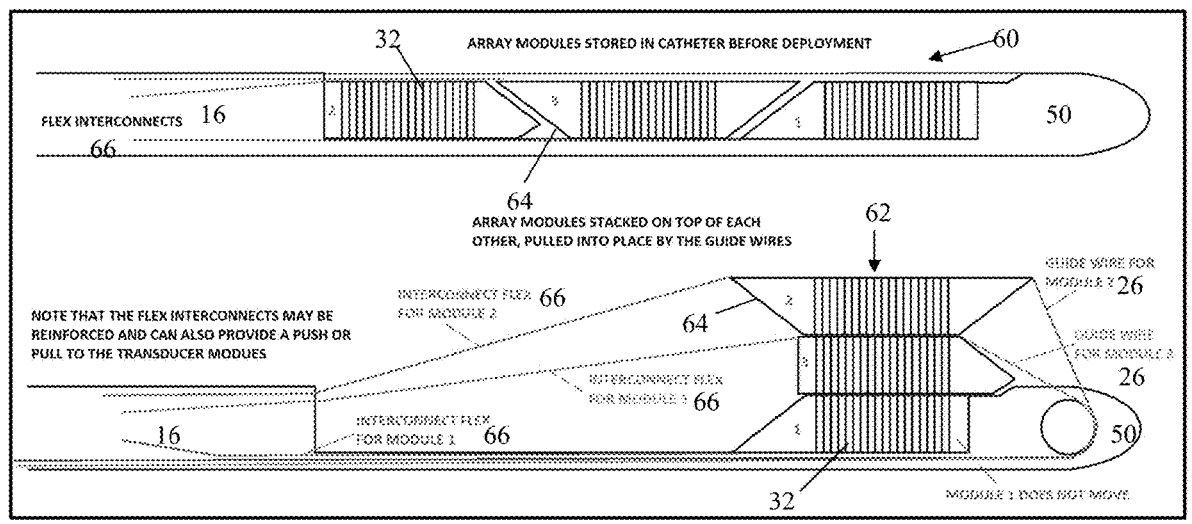
FIG. 5 illustrates another embodiment for rearranging segments of a transducer to form two different apertures for imaging.

The array 12 is formed from multiple sub-arrays or segments 32. Any number of segments may be used, such as two, three, four, five, or more. FIGS. 2-4 show an embodiment with four segments, and FIG. 5 shows an embodiment with three segments.

These transducer segments 32 are arrays of elements 24. Each segment 32 is of a same size, shape, and same number of elements 24 as other segments 32. For example, four segments 32 are provided and each segment 32 has a rectangular shape of array of 48×12 elements, forming a 7.2×1.8 mm$^2$ multi-dimensional or two-dimensional (2D) sub-array. Other sizes and/or element distributions may be used. The element pitch is 150 microns in azimuth and elevation, but other pitches may be used. The segments 32 are configured to operate at a center frequency of 3.5-4 MHz with a wide bandwidth that enables harmonic 5 MHz or 6 MHz, but other frequencies of operation with or without harmonic may be used. In alternative embodiments, different segments 32 have different numbers of elements, sizes, shapes, and/or frequencies of operation.

In one embodiment, each segment 32 includes a receive beamformer for partial or subarray beamformation. For example, a beamformer application specific integrated circuit connects with one of the segments 32 for beamforming from 576 elements to 24 or 48 outputs of partially beamformed data so that the four segments 32 provide 96 or 192 channels to the beamformer 52 of the ultrasound system.

The elements 24 of the segments 32 electrically connect to the conductors 16. Loose wires and/or flexible circuits with traces connect the electrodes of the elements 24 and/or outputs of subarray beamformers to the conductors 16. Each segment 32 may separately connect to the conductors 16. Alternatively, a daisy-chain approach is used where signals from an end segment 32 are passed to the next segment 32, which passes to the next segment 32 and so on until connecting to the conductors 16.

The housing 50 includes a guide 36. The guide 36 is a groove, rail, chain, pulley, or other arrangement for mechanically guiding the pins 38 along the housing 50. The guide 36 is on an interior of the housing 50. The guide 36 may be a groove in the housing itself or may be a structure supported or attached to the interior of the housing 50. The guide 36 allows some or all of the pins 38 to slide longitudinally in the housing 50. This sliding allows for reconfiguration of the array 12 by allowing the segments 32 to take different positions relative to each other. One or more pins 38 may be fixed in place relative to the housing 50.

The guide 36 may be formed by two parallel structures, such as shown by the dashed lines in FIG. 3. The guide 36 may be a single groove or structure in other embodiments.

The pegs or pins 38 are metal, plastic, or other materials. A wheel, gear, or ball bearing structure for mating with the guide 36 while allowing for sliding along the guide 36 may be provided. Alternatively, the pins 38 fit and slide in the guide 36 without wheels or rotatable structures.

Each segment 32 includes one or more pins 38 at one end of the segment 32. The pins 38 extend from a frame or holder connected to the elements 24 of the segment 32. Alternatively, the pins 38 extend from or are surrounded by elements 24.

The segments 32 may be connected by springs 34 or other flexible connectors. The ends of the segments 32 opposite the pins 38 are connected by springs 34. The ends of the segments 32 with pins 38 may be connected by springs 34. Similarly, the ends of the end segments 32 may include springs 34 connected with the housing 50.

The springs 34 are metal springs, elastic material, and/or shaped (superelastic) alloy that seeks to return to a given shape. Spring interconnects provide greater flexibility within the acoustically active part for improved maneuverability. Where the segments 32 are displaced by sliding in the guide 36, the springs 34 apply pressure to return the segments 32 to an original or other arrangement by sliding back.

A guide wire 26 connects to one or more of the segments 32 to slide the segment 32 along the guide 36. For example, a guide wire 26 connects to the pin holder of the segment 32 nearest to the handle or nearest the tip of the probe 18. By pulling on the wire 26, the segment 32 slides in the guide 36. The springs 34 cause the other segments 32 to also slide on the guide 36, except for the last segment 32 where the pin 38 is fixed to the housing 50 or guide 36. To return the segments 32 to a different or original aperture shape, the guide wire 26 is released or moved in the opposite direction. The springs 34 with or without force from the guide wire 26 cause some of the segments 32 to slide along the guide 36. The segments 32 return to the original aperture. The guide wire 26 is a control wire for sliding the multi-element transducers relative to each other.

Other mechanical and/or manual activations for rearranging the segments 32 may be used. In other embodiments, electromechanical activation is provided. A motor causes the segments 32 to slide along the guide 36. The sliding is actuated by piezoelectric or electromagnetic motors located near the transducer or array 12. The motors are controlled electronically from the probe handle. Actuating rods may be used instead of or with the guide wire 26. Actuating rods may be used in a rotating manner, push-pull manner, or both.

When the user or a motor pulls on the most distal or proximal peg 38, the imaging transducers or segments 32 move. The segments 32 are slidable and/or rotatable relative to each other within the housing 50. The segments 32 move against resistance offered by one of the pegs 38 being fixed in place. By sliding along the guide 36, the segments 32 may be arranged or configured to form different apertures. A lock may engage to hold the segments 32 in place in either or both the apertures. Both apertures may be used to image a same patient. For example, the reconfiguration occurs while the array 12 and part of the housing 50 are within the patient.

FIGS. 2-4 show formation of two different apertures, one long and narrow for moving through the lumen and the other more symmetric along azimuth and elevation for volume or multi-planar imaging. The aspect ratio of the array 12 or transducer changes from a longer, narrower profile to a rectangular or squarer profile through sliding of the non-folding segments 32.

FIGS. 2 and 3 show top and side views of the segments 32 as arranged for insertion of the probe 18 into the patient and/or for moving the array 12 through a lumen of the patient. In FIG. 2, the transmit and receive direction (depth) for acoustic energy of each segment 32 is into or out of the drawing sheet. In FIG. 3, the transmit and receive direction (depth) for the acoustic energy is periductular to the top long edge of each segment 32 within the plane of the drawing sheet. In this example arrangement, alternate segments 32 are angled at 18-degrees and 162-degrees with the catheter body length. Other angles may be used. For example, the segments 32 may be in a same plane so the angle is 0 degrees. The elements 24 of the segments form a long (e.g., 192 element) and narrow (e.g., 12 element) aperture from the four segments. For example, the aperture is more than 27.4 mm long and 2.3 mm wide. The holders and springs 34 may separate the parts of the array 12 so the aperture formed from multiple segments 32 may not be continuous. Where non-zero angle is used, then a single segment 32 may be used for planar imaging where the plane extends from the probe 18 at the angle of the segment 32 to the long axis of the probe 18. Alternatively, multiple of the segments are used with the angles and gaps accounted for in electronic beamformation. This relatively long and narrow arrangement of the segments 32 allows the probe 18 to be long, thin, and flexible for ease of intravascular insertion and placement.

In one embodiment, the rectangular segments 32 form 2D arrays or sub-arrays with shorter ends and longer sides. For insertion, the segments 32 are generally short-end to short-end adjacent (see FIGS. 2 and 3), forming a longer array 12 with the same width (short end width) as the segments 32. By sliding the pegs 38 in the guide 36, the aperture used in imaging may be mechanically rearranged. FIG. 4 shows an example. This additional aperture is formed by placing the longer edges of the segments 32 adjacent to each other instead of the short ends. By pulling or pushing the peg or pin ends of the segments 32 together, a more symmetric, square, or more similar azimuth and elevation dimension aperture is available. The transducers slide into a more square-like aperture.

In the example of FIG. 4, a square aperture is provided to so that the quality of imaging is the same in both azimuth and elevation. The aperture is formed by placing the four segments 32 side-by-side on the long sides with little (e.g., 2 or less elements) to no gaps between the segments, providing an approximately 7.2×7.2 mm$^2$ array 12 in one embodiment. One dimension (e.g., azimuth) has a same length as the segments 32 (shown as vertical in FIG. 4), and the other dimension (e.g., elevation) has a same length as the length of the segments 32 but is formed by four short ends widths (shown as horizontal in FIG. 4). The segments 32 are rearranged to provide a 2D array 12 with greater width or elevation than the array 12 provided by short-end to short-end of FIG. 2. Other rectangular but more square-like (width more similar to length or elevation more similar to azimuth) arrays 12 formed by the segments 32 may be provided.

The sliding of one or more segments 32 relative to the other causes the segments 32 to create a more square-like or symmetrical in 2D profile for 3D, volume, or multi-planar imaging. For example, once insertion is complete, the array 12 is reconfigured from the insertion arrangement of long and narrow (see FIGS. 2 and 3) to the array 12 for volume imaging. In a cardiac example, the 2D array 12 of FIG. 4 is used inside a cardiac chamber while the array 12 of FIGS. 2 and 3 is used during guidance or insertion to place the array 12 into the chamber. Once in the chamber, this wide, squarer matrix transducer, similar to a transesophageal probe, is provided despite having had to pass through narrow and tortuous vascular pathways. The retractable transducer segments 32 can create a more square-like profile for 3D volume imaging while not hindering insertion or traveling in the lumen.

The expandable portion 30 inflates, stretches, or expands to allow the reconfiguration of the array 12. By using force from the segments 32, pumped in fluid (e.g., saline), or another mechanical arrangement, the expandable portion 30 expands to allow room for the array 12. The expansion occurs before and/or while reconfiguring the array 12. In the example of FIG. 4, the expandable portion 30 is a balloon inflated with saline. The pins 38 are slid in the guide 36 to form the array 12 in the volume imaging aperture in the previously inflated balloon (e.g., balloon is orthogonal to the plane of the drawing).

FIG. 5 shows another embodiment for slidable rearrangement of the segments 32 between a relatively long and narrow aperture 60 and a more square-like or less long and wider aperture 62. Each segment 32 has at least one angled surface 64 mated with another angled surface 64 of an adjacent segment 32. Any angle may be used, such as about 45 degrees. Multiple angled surfaces 64 on one end of one segment 32 may be provided. The angled surfaces 64 guide the segments 32 to stack and unstack as force from one or more guide wires 26 is applied. The long narrow aperture 60 is formed for insertion by the segments 32 aligned end-to-end (short end adjacent), and the more square-like volume imaging aperture 62 is formed by the segments 32 stacked long-side to long-side. The angled surfaces 64 adjacent to each other cause the segments 32 to slide against each other for transition between the two apertures 60, 62. The angled surfaces 64 allow for sliding to form the apertures 60, 62.

In one embodiment, the segments 32 can be configured into a two-dimensional array 12 by sliding the segments 32 into place from a storage pocket within the probe. The mechanical action is controlled by guide wires 26 pulled from the handle of the probe. The interconnect flexes 66 forming at least part of the conductors 16 are also combined with a laminated-on strength member, such as a Kevlar weave or even a very thin, spring like, metal. The guide wires 26 pull the segments 32 into place and keep them under tension while imaging. Tension is also provided by the interconnects flexes 66. When the procedure is finished, the guide wires 26 loosen and the interconnect flexes 66 pull the segments 32 back into place, forming the long narrow aperture 60. The guide wires 26 may instead be additional reinforced flex interconnects, doubling the number of electrical interconnects to the segments 32.

By having one segment 32 (e.g., module 1) fixed in place, this segment 32 may always be used for imaging, even when the volume imaging aperture 62 is not deployed. For example, while guiding the probe 18 (e.g., catheter into the heart), this segment 32 (e.g., module 1) or multiple segments 32 in the in-line state (e.g., top of FIG. 5) may be used in the long narrow aperture 60. The expandable portion 30 may be a balloon filled with a non-toxic grease or hydrogel that provides mechanical lubricity as well as an acoustic couplant between the transducer segments 32 and the outside environment of the patient.

Figure 6:
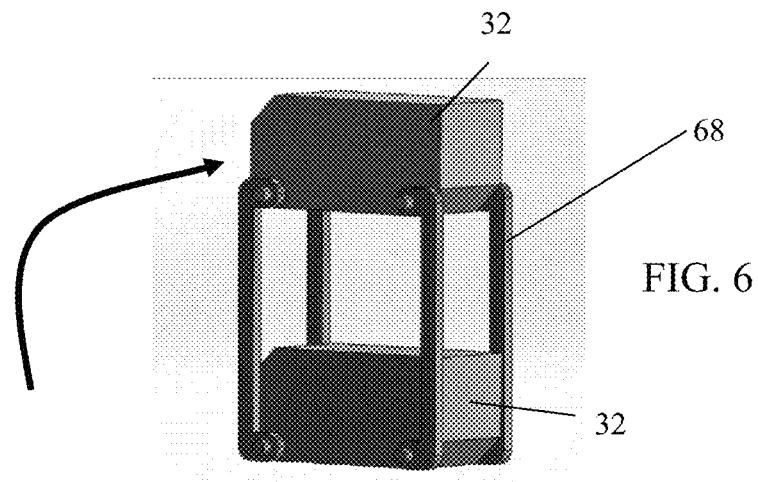
FIG. 6 is a perspective view of an armature arrangement for rearranging segments of a transducer according to one embodiment.

In other embodiments, other structures are provided to guide the segments 32 relative to each other for stacking and unstacking or rearranging between two different apertures. FIG. 6 shows an example where arms 68 rotatably connect between two or more segments 32. The arms 68 pivotably connect to the different segments 32. Any number, such as four, parallel arms 68 connect between any two or more given segments 32. The arms 68 rotate to assist the top segment 32 in getting into place and remaining parallel to the bottom segment 32. One or more segments 32 may then slide between the segments 32 connected with the arms 68. Guide wires 26 or other pushing or pulling arrangements may actuate the mechanism.

One or more sensors 74 may be provided to sense formation of the either or both apertures 60, 62. FIG. 4 shows an example where a contact sensor 74 senses the segments 32 as arranged for the volume imaging aperture. Other types of sensors may be used, such as current, resistive, optical, infrared, magnetic position, Hall effect, GMR, inductive, or capacitive sensors. The sensor or sensors 74 may be separate from or incorporated into the segments 32. The sensor 74 is a position sensing device so that the aperture formation is detected and communicated to a user interface or processor controlling imaging. The sensor 74 may measure the relative offset between each transducer segment 32. The offset may be used to make adjustments to the beamforming to account for any gaps in the aperture 60, 62 due to use of the different segments 32.

Figure 7:
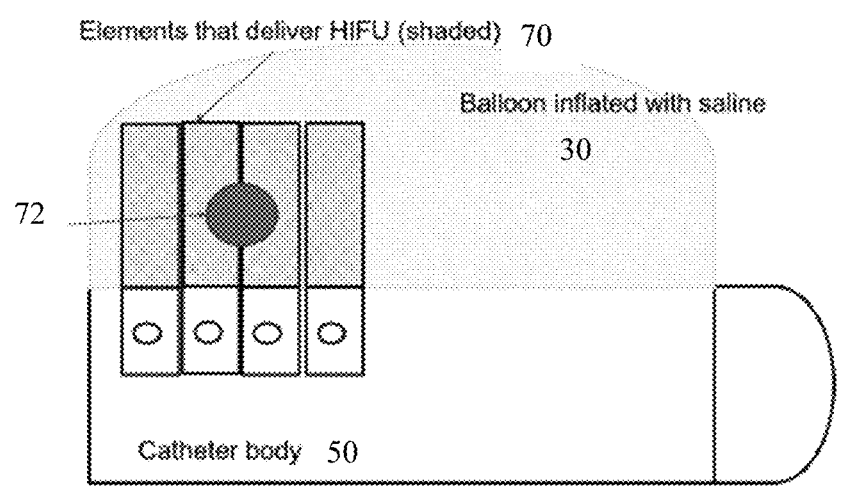
FIG. 7 illustrates an embodiment of a segmented transducer arranged for high intensity focused ultrasound (HIFU)

FIG. 7 shows another embodiment for use in HIFU. The structures of FIGS. 2-4 are used. The segments 32 have elements with high "Q" for transmission of higher acoustic energy and/or longer pulses for HIFU. Two segments 32 may have only the HIFU transmission elements. Two other segments 32 include both the HIFU transmission elements as well as elements for ultrasound imaging, such as for M-mode imaging at higher frequencies without steering. For example, the two inner segments 32 form the M-mode imaging array 72 surrounded by the HIFU array 70 formed by all four segments 32. The HIFU elements may be fixed focus at Rayleigh distance of a center transducer. The HIFU may be used for treatment, such as ablation of the heart or pancreas.

Referring again to FIG. 1, the beamformer 52 electronically focuses along the azimuth and/or elevation directions. A plurality of scan lines using an aperture is scanned. During receive operations, the focus may vary as a function of depth (i.e., dynamic focusing).

The image processor 54 is a detector, filter, processor, application specific integrated circuit, field programmable gate array, digital signal processor, control processor, scan converter, three-dimensional image processor, graphics processing unit, analog circuit, digital circuit, or combinations thereof. The image processor 54 receives beamformed data and generates images on the display 56. The images are associated with a two-dimensional scan during insertion using at least part of the long narrow aperture. The images are associated with a three-dimensional scan after insertion using the more symmetric volume imaging aperture. Data representing a volume is acquired by scanning, and an image is rendered from the 3D scan.

Figure 8:
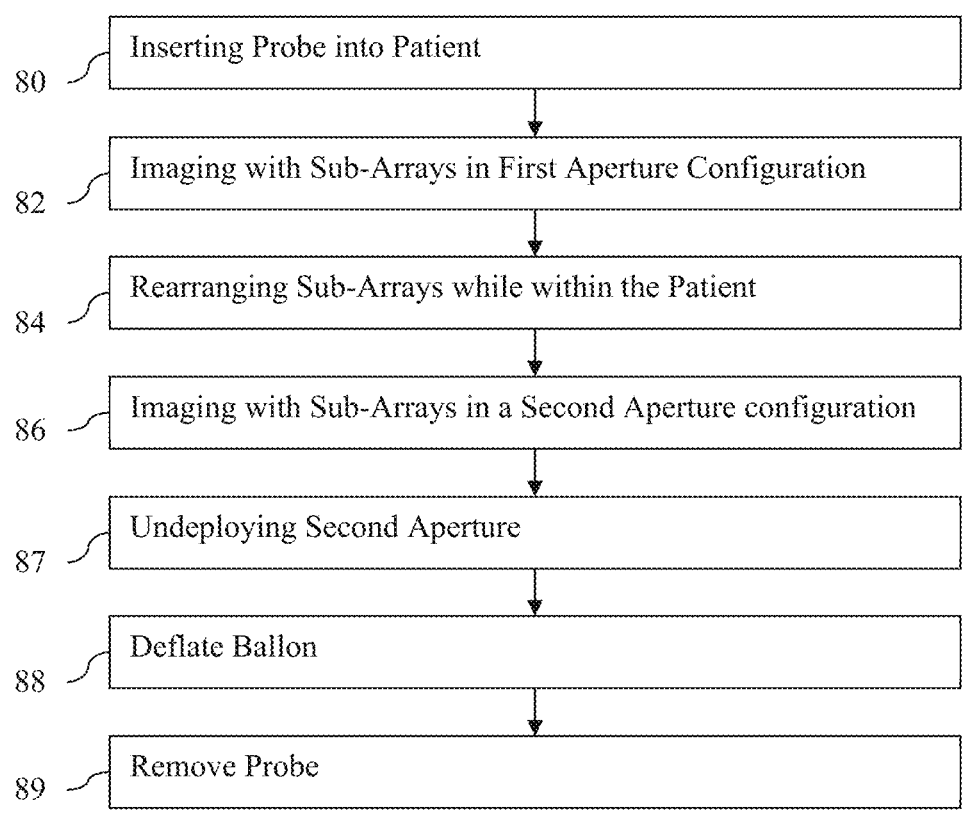
FIG. 8 is a flow chart diagram of one embodiment of a method for ultrasound imaging with a configurable array in an intraluminal probe.

FIG. 8 is a flow chart diagram of one embodiment of a method for ultrasound imaging with an endoluminal ultrasound probe. Slidable sub-arrays in the probe are used to image with two different apertures. The probes of FIGS. 2-5 and 7 or other intraluminal probes with slidable sub-arrays are used to image with different apertures from within the patient.

Additional, different, or fewer acts may be provided. For example, acts for configuring the ultrasound imaging system and/or acts for diagnosis or treatment are included. The acts are performed in the order shown or a different order.

In act 80, the intraluminal probe is inserted into a patient. The probe is inserted into a lumen, such as a blood vessel. For example, the probe is an intra-cardiac catheter.

The intraluminal probe includes at least two sub-arrays. The two sub-arrays are separate devices that may be moved relative to each other. The two sub-arrays are positioned for insertion in a way that avoids bulges or other interference with the probe moving in the lumen in the patient and/or with the probe entering the patient. For example, the two sub-arrays are positioned short-end to short-end, forming a long and narrow arrangement with a width of 3, 5, or 10 mm or less. For other types of probes, the width may be greater, such as 25 mm or less.

In act 82, one or more of the sub-arrays are used to image the patient. The sub-arrays form an aperture extending more along the length of the probe than along the width. For example, the sub-arrays are short-end to short-end during insertion. One, multiple, or all of the sub-arrays connect with the beamformer to form an aperture for 2D imaging.

In the arrangement of FIG. 2, one or more of the sub-arrays are at a non-zero angle to the length of the probe. The angle results in the imaging plane being at the angle to the length of the probe. In other embodiments, the angle is zero or the beamformer steers to scan in a plane along the length of the probe. Where the sub-arrays are aligned at the zero angle (see FIG. 5) or where beamforming is used to account for different angles, the aperture used for imaging may include more than one sub-array.

Images are generated to assist in insertion. By scanning using the aperture for insertion, two-dimensional images are generated.

In act 84, the two sub-arrays are rearranged. Using manual or motorized force, one or more of the sub-arrays are slid within the probe. For example, a control wire is pushed or pulled.

One or more sub-arrays slide relative to other sub-arrays, such as relative to each other. The rearrangement is from an aperture formed for imaging during insertion to an aperture for imaging once the probe is placed within the patient. For example, once the tip of the probe is within a heart chamber, the sub-arrays are rearranged into another aperture for volume imaging.

The rearrangement may move the sub-arrays to stack them or rotate them to align along long sides instead of short sides. For example, the angles of the sub-arrays of FIG. 5 are used to stack the arrays. As another example, the pegs in the guides cause the segments of FIGS. 2 and 3 to rotate against each other forming the array of FIG. 4.

The probe housing may be expanded due to or to allow the rearrangement. For example, fluid is pumped into the housing of the probe at an expandable portion, such as a balloon. The added fluid causes the expandable portion to extend out into the patient, creating more room for the larger or wider aperture formed by the rearrangement of the sub-arrays.

In act 86, multiple of the sub-arrays are used to image the patient. The sub-arrays form an aperture wider than the probe during insertion. The increased width allows for volume scanning and imaging. For example, the sub-arrays are stacked with longest sides adjacent each other, such as shown in FIGS. 4 and 5.

The sub-arrays connect with the beamformer to form an aperture for volume, 3D, or multi-planar imaging. The aperture is used for volume scanning. Images are generated to assist in diagnosis and/or treatment. By scanning using the aperture for volume imaging, images rendered from 3D are generated.

In act 87, the second aperture is undeployed. The sub-arrays are rearranged to form the first aperture. Spring force, force applied by the control wire, or other force rearranges the sub-arrays to return the arrangement of act 82.

In act 88, the balloon or expandable portion of the housing is deflated or flattened. The probe may then be removed in act 89.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound probe for ultrasound imaging, the ultrasound probe comprising:
a housing configured for insertion into a patient, the housing having an expandable portion;
a guide within the housing;
a first two-dimensional array of elements connected with the guide; and
a second two-dimensional array of elements connected with the guide,
wherein the first two-dimensional array is slidable along the guide relative to the second two-dimensional array to form first and second imaging apertures of the ultrasound imaging while the housing and the first and second two-dimensional arrays are within the patient,
wherein the first imaging aperture is longer and narrower than the second imaging aperture, and
wherein the first two-dimensional array of elements and the second two-dimensional array of elements are stacked to form the second imaging aperture.

2. The ultrasound probe of claim 1 wherein the housing comprises an expandable portion adjacent to the first and second two-dimensional arrays, wherein the first imaging aperture is within the housing without expansion of the expandable portion and wherein the second imaging aperture is within the housing with expansion of the expandable portion.

3. The ultrasound probe of claim 1 wherein a first end of the first two-dimensional array connects to the guide with a first pin, and a first end of the second two-dimensional arrays connect with the guide with a second pin, and wherein a spring connects the first two-dimensional array to the second two-dimensional array, the spring connected at a second end of the first two-dimensional array and a second end of the second two-dimensional array.

4. The ultrasound probe of claim 1 wherein the first and second two-dimensional arrays comprise rectangular arrays each with ends shorter than sides, the first imaging aperture has one of the ends of the first two-dimensional array adjacent to one of the ends of the second two-dimensional array, and the second imaging aperture has one of the sides of the first two-dimensional array adjacent to one of the sides of the second two-dimensional array.

5. The ultrasound probe of claim 4 wherein the second imaging aperture comprises a square or rectangular shape having a length of the side of the first two-dimensional array and a width of at least a sum of lengths of ends of both the first and second two-dimensional arrays.

6. The ultrasound probe of claim 1 further comprising a wire connected to at least the first two-dimensional array to slide the first two-dimensional array along the guide.

7. The ultrasound probe of claim 1 further comprising third and fourth two-dimensional arrays, wherein the second imaging aperture comprises the first, second, third, and fourth arrays placed side-by-side.

8. The ultrasound probe of claim 1 wherein the first imaging aperture has a longest axis of the first and second two-dimensional arrays positioned at different non-zero angles to a length axis of the housing.

9. The ultrasound probe of claim 1 further comprising wires connecting to electrodes of the first two-dimensional array and electrodes of the second two-dimensional arrays.

10. The ultrasound probe of claim 1 wherein the first two-dimensional array has a first angled surface and the second two-dimensional array has a second angled surface, the first and second angled surfaces adjacent each other to cause the first two-dimensional array to stack with the second two-dimensional array by sliding the first angled surface along the second angled surface.

11. The ultrasound probe of claim 1 wherein the first and second two-dimensional arrays connect to each other pivotably by parallel arms.

12. The ultrasound probe of claim 1 further comprising a sensor configured to sense formation of the second imaging aperture and/or formation of the first imaging aperture.

13. An ultrasound array for a catheter or intraluminal probe, the ultrasound array comprising:
a housing configured for insertion into a patient; and
a plurality of multi-element transducers slidable relative to each other within the housing, the plurality multi-element transducers configurable in first and second imaging apertures while within the patient, the first imaging aperture shaped differently than the second imaging aperture, the first imaging aperture formed by sliding from the plurality of multi-element transducers arranged in the second imaging aperture,
wherein the plurality of multi-element transducers are stacked to form the second imaging aperture, the second aperture being wider than each of the plurality of multi-element transducers and the first aperture being longer than each of the plurality of multi-element transducers.

14. The ultrasound array of claim 13 wherein the housing includes a balloon section where fluid inflates the balloon section for the second imaging aperture, and a control wire connected to at least one of the multi-element transducers, the control wire configured to slide the multi-element transducers relative to each other.

15. The ultrasound array of claim 13 wherein the plurality of multi-element transducers have adjacent angled surfaces to guide the plurality of multi-element transducers to stack.

16. An ultrasound array for a catheter or intraluminal probe, the ultrasound array comprising:
a housing configured for insertion into a patient; and
a plurality of multi-element transducers slidable relative to each other within the housing, the plurality of multi-element transducers configurable in first and second imaging apertures while within the patient, the first imaging aperture shaped differently than the second imaging aperture, the first imaging aperture formed by sliding from the plurality of multi-element transducers arranged in the second imaging aperture,
wherein the plurality of multi-element transducers are stacked to form the second imaging aperture.

* * * * *